(12) United States Patent
Raines

(10) Patent No.: US 10,342,578 B2
(45) Date of Patent: Jul. 9, 2019

(54) PADDLE LEAD DELIVERY TOOLS

(71) Applicant: PACESETTER, INC., Sylmar, CA (US)

(72) Inventor: Aaron Raines, Dallas, TX (US)

(73) Assignee: PACESETTER, INC., Sylmar, CA (US)

( * ) Notice: Subject to any disclaimer, the term of this patent is extended or adjusted under 35 U.S.C. 154(b) by 27 days.

(21) Appl. No.: 15/637,948

(22) Filed: Jun. 29, 2017

(65) Prior Publication Data

US 2019/0000508 A1 Jan. 3, 2019

(51) Int. Cl.
*A61B 17/34* (2006.01)
*A61N 1/05* (2006.01)
*A61B 17/00* (2006.01)

(52) U.S. Cl.
CPC ........ *A61B 17/3468* (2013.01); *A61N 1/0553* (2013.01); *A61N 1/0558* (2013.01); *A61B 2017/00309* (2013.01)

(58) Field of Classification Search
CPC ................ A61N 1/0553; A61N 1/0558; A61B 2017/00309; A61B 17/3468
See application file for complete search history.

(56) References Cited

U.S. PATENT DOCUMENTS

| 6,666,866 | B2 | 10/2003 | Martz et al. |
| 8,781,574 | B2 | 7/2014 | Pless et al. |
| 2005/0049663 | A1* | 3/2005 | Harris ............... A61B 17/34 607/115 |
| 2013/0289685 | A1 | 10/2013 | Browne et al. |

* cited by examiner

*Primary Examiner* — Alyssa M Alter

(57) ABSTRACT

A delivery tool is provided for use in implanting a paddle lead including a paddle electrode array disposed at a distal end of a paddle lead body. The delivery tool has a proximal tool end and a distal tool end opposite the proximal end and a tool body extending therebetween. The tool body is adapted to receive a portion of the paddle lead body and includes a longitudinal member extending along the tool body and a plurality of structural members extending from the longitudinal member. The structural members are distributed along the longitudinal member such that gaps are defined between longitudinally adjacent structural members. The tool body is structured to have increased resistance to bending in a first direction and reduced resistance to bending in a second direction perpendicular to the first direction.

20 Claims, 19 Drawing Sheets

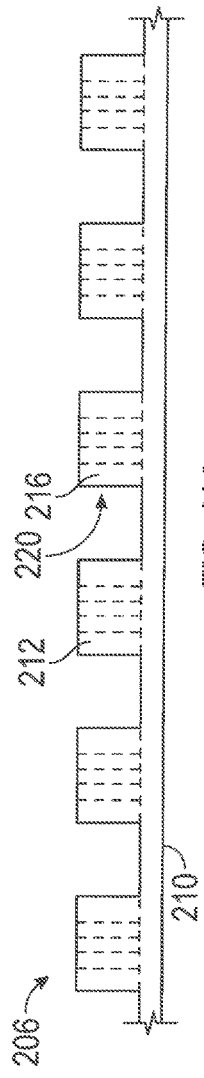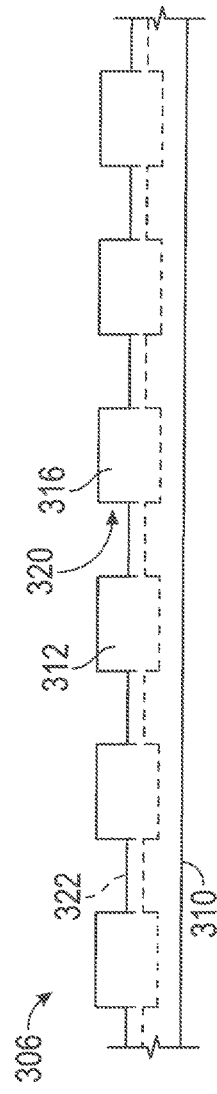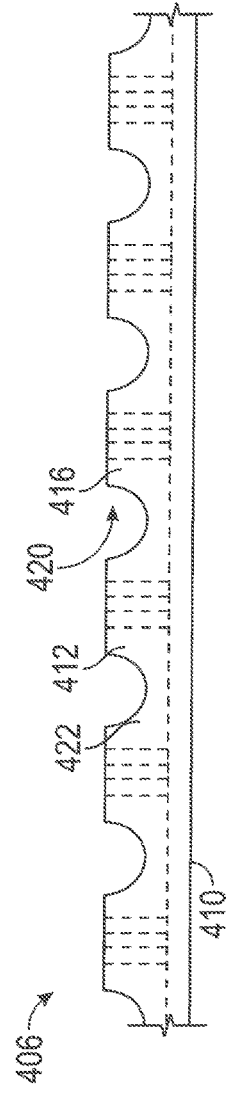

US 10,342,578 B2

PADDLE LEAD DELIVERY TOOLS

TECHNICAL FIELD

Aspects of the present disclosure relate to apparatuses, systems, and methods for deploying implantable medical devices and more particularly to delivery tools for implanting paddle leads for electrical stimulation of nerve or tissue in a patient.

BACKGROUND

Application of electrical fields to spinal nerve roots, spinal cord, and other nerve bundles for the purpose of chronic pain control has been actively practiced for some time. While a precise understanding of the interaction between applied electrical energy and the neural tissue is not understood, application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to regions of the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Each exterior region, or each dermatome, of the human body is associated with a particular spinal nerve root at a particular longitudinal spinal position. As illustrated in FIG. 1, the head and neck regions are associated with C2-C8, the back regions extend from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. For example, to address chronic pain sensations that commonly focus on the lower back and lower extremities using conventional techniques, a specific energy field is typically applied to a region between vertebrae levels T8 and T12. The specific energy field often stimulates a number of nerve fibers and structures of the spinal cord. By applying energy in this manner, the patient commonly experiences paresthesia over a relatively wide region of the patient's body from the lower back to the lower extremities.

Positioning of an applied electrical field relative to a physiological midline is also important. Nerve fibers extend between the brain and a nerve root along the same side of the dorsal column that the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral". Accordingly, bilateral pain is addressed through application of electrical energy along both sides of the column and/or along a patient's physiological midline.

Implantable leads have conductors extending there through that place distal electrodes of the lead in electrical communication with implantable pulse generators (IPGs) from which the implantable leads distally extend. The distal electrodes of the leads are positioned adjacent to pertinent nerves such that the electrodes deliver stimulation pulses to the nerves, those stimulation pulses originating from the IPGs and transmitted to the distal electrodes via the conductors of the leads.

To supply suitable pain-managing electrical energy, multi-programmable IPGs enable a pattern of electrical pulses to be varied across the electrodes of a lead. Specifically, such systems enable electrodes of a connected stimulation lead to be set as an anode (+), as a cathode (−), or to a high-impedance state (OFF). As is well known, negatively charged ions and free electrons flow away from a cathode toward an anode. Consequently, a range of very simple to very complex electrical fields can be created by defining different electrodes in various combinations of (+), (−), and OFF. Of course, in any instance, a functional combination must include at least one anode and at least one cathode (although in some cases, the "can" of the IPG can function as an anode).

Percutaneous leads and paddle leads are the two most common types of lead designs that provide conductors to deliver stimulation pulses from an implantable pulse generator (IPG) to distal electrodes adjacent to the pertinent nerve tissue. Example commercially available leads include the QUATTRODE™, OCTRODE™, LAMITRODE™, TRIPOLE™, EXCLAIM™, and PENTA™ stimulation leads from Abbott™.

A conventional percutaneous lead includes electrodes that substantially conform to the body of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

A conventional paddle lead has a paddle configuration and typically possesses a plurality of electrodes (commonly, eight, or sixteen) arranged in columns. Due to their dimensions and physical characteristics, conventional paddle leads may require a surgical procedure (a partial laminectomy) for implantation. Multi-column paddle leads enable more reliable positioning of a plurality of electrodes as compared to percutaneous leads. Also, paddle leads offer a more stable platform that tends to migrate less after implantation. Paddle leads are capable of being sutured in place. Paddle leads also create a unidirectional electrical field and, hence, can be used in a more electrically efficient manner than at least some known percutaneous leads.

Conventional delivery of paddle leads generally requires large incisions and substantial removal of lamina, resulting in trauma to the patient and longer procedure time. As such, there is a need for apparatuses, systems, and methods for delivering large, multi-electrode paddle leads in a minimally invasive surgical approach with minimal vertebral displacement. It is with these observations in mind, among others, that various aspects of the present disclosure were conceived and developed.

SUMMARY

Implementations described and claimed herein address the foregoing problems, among others, by providing apparatuses, systems, and methods for paddle lead implantation. In one implementation, a delivery tool for paddle lead implantation includes a tool body extending between a proximal tool end and a distal tool end opposite the proximal tool end. The tool body is adapted to receive a portion of a paddle lead body of the paddle lead. The tool body includes a longitudinal member extending along the tool body and a plurality of structural members extending from the longitudinal member. The plurality of structural members is distributed along the longitudinal member such that gaps are defined between adjacent structural members. In one implementation, the longitudinal member and plurality of structural members are adapted to have a first resistance to bending along a first plane and a second resistance, less than the first resistance, to bending along a second plane that is perpendicular to the first plane.

In another implementation, the tool body includes a second longitudinal member such that the first and second longitudinal members extend along opposite lateral sides of the tool body and the structural members extend laterally between the longitudinal members. In such implementations of the present disclosure, a first and second set of the structural members may extend across opposite sides of the tool body. One or more of the structural members may also include a gripping feature including, without limitation, one or more of a protrusion, a groove, and a roughened surface.

In yet another implementation, the longitudinal member includes a first lateral edge along which a first set of the structural members is longitudinally distributed. The longitudinal member further includes a second lateral edge opposite the first lateral edge along which a second set of the structural members is disposed. In such implementations, one of a lateral rib or a web having a height less than the structural members may extend between adjacent structural members.

In another implementation, the tool body comprises at least one of polypropylene, polyethylene, acrylonitrile butadiene styrene, or Nitinol.

In still another implementation, the delivery tool includes a lead retention feature disposed at the proximal tool end, the lead retention feature adapted to engage a portion of the paddle lead body. In certain implementations, the lead retention feature includes a body adapted to receive the portion of the paddle lead body and that defines a hole. The lead retention feature further includes a tab having a protrusion and a hinge coupling the tab to the body. As such, the lead retention feature is adapted to transition between an engaged configuration in which the protrusion is inserted into the hole and a disengage configuration in which the protrusion is removed from the hole. In an alternative implementation, the lead retention feature includes a set of walls defining an inlet, an outlet, and a lead path extending therebetween and along which the paddle lead body may be made to follow in order to retain the paddle lead body. The proximal tool end may include a handle coupled to the tool body.

In another implementation, the lead delivery tool includes a paddle retention feature disposed at the distal tool end. The paddle retention feature is adapted to receive a paddle electrode array of the paddle lead. In certain implementations, the paddle retention feature defines a slot into which the paddle electrode array may be inserted and retained by way of an interference fit.

In another embodiment, a delivery tool for use in implanting a paddle lead is provided. The delivery tool includes a proximal tool end and a distal tool end opposite the proximal tool end and comprises a tool body extending therebetween. The tool body includes a plurality of structural members adapted to have a first resistance to bending of the tool body in a first plane and to have a second resistance, less than the first resistance, to bending along a second plane perpendicular to the first plane.

In one implementation, the delivery tool includes a lead retention feature disposed at the proximal tool end and coupled to the tool body. The lead retention feature is adapted to retain and fix the position of a portion of the paddle lead relative to the tool body. In another implementation, the delivery tool includes a paddle retention feature disposed at the distal tool end and adapted to retain a paddle electrode array of the paddle lead.

In yet another implementation, the plurality of structural members includes a first and second set of structural members. The first set of structural members is disposed in a first section of the tool body and adapted to have a third resistance to bending in a first bending direction along the second plane. The second set of structural members is disposed in a second section of the tool body proximal the first section. The second set of structural members is adapted to have a fourth resistance to bending in a second bending direction opposite the first bending direction and each of the third and fourth resistances being less than the first resistance.

In still another implementation, the plurality of structural members is longitudinally distributed along the tool body and a bending range of the tool body along the second plane is limited by contact between adjacent structural members.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 11A is a side view of the paddle lead delivery tool of FIG. 9.

FIGS. 11B and 11C are, respectively a side view of first alternative tool body and a second alternative tool body for use with the paddle lead delivery tool of FIG. 9.

DETAILED DESCRIPTION

Aspects of the present disclosure involve apparatuses, systems, and methods for paddle lead implantation. Generally, a paddle lead tool deploys a paddle lead into the epidural space. The lead delivery tool is adapted to resist bending in a first plane and compression along a longitudinal axis while facilitating bending in a second plane perpendicular to the first plane. In use, the tool may be oriented relative to the patient such that the first plane aligns with a medial lateral ("ML") or coronal plane of the patient and the second plane aligns with an anterior-posterior ("AP") or sagittal plane of the patient. The flexibility of the lead delivery tool enables, among other things, the lead delivery tool to be arranged in multibend or "s-shaped" configurations. During implantation, a first portion of the lead delivery tool coupled to an electrode array of the paddle lead may be disposed within the patient while a second portion of the lead delivery tool may be positioned outside the patient. The directional flexibility of the lead delivery tool allows the relative angle between the first and second portions to be reduced, thereby improving the transfer of longitudinal forces applied to the second portion to the first portion. In certain applications, the flexibility may even permit the second portion of the lead delivery tool to be substantially parallel to the first portion of the lead delivery tool.

As such, the apparatuses, systems, and methods disclosed herein involve a smaller incision and minimal vertebral displacement, thereby increasing safety, reducing trauma to the patient, minimizing damage to the dura and adjacent tissues, and decreasing procedure time, among other advantages.

Figure 1:
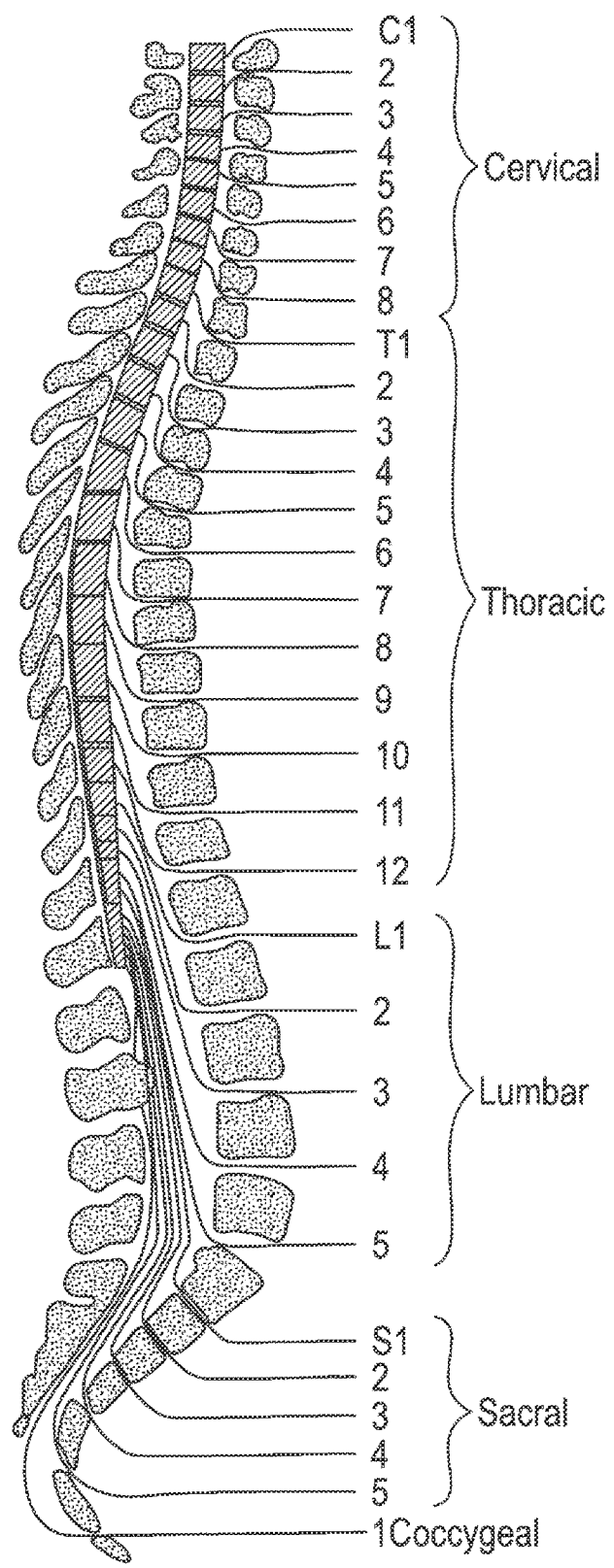
FIG. 1 is a schematic diagram of the spinal cord and the nerve roots in relation to the vertebral spinal canal.
Figure 2A:
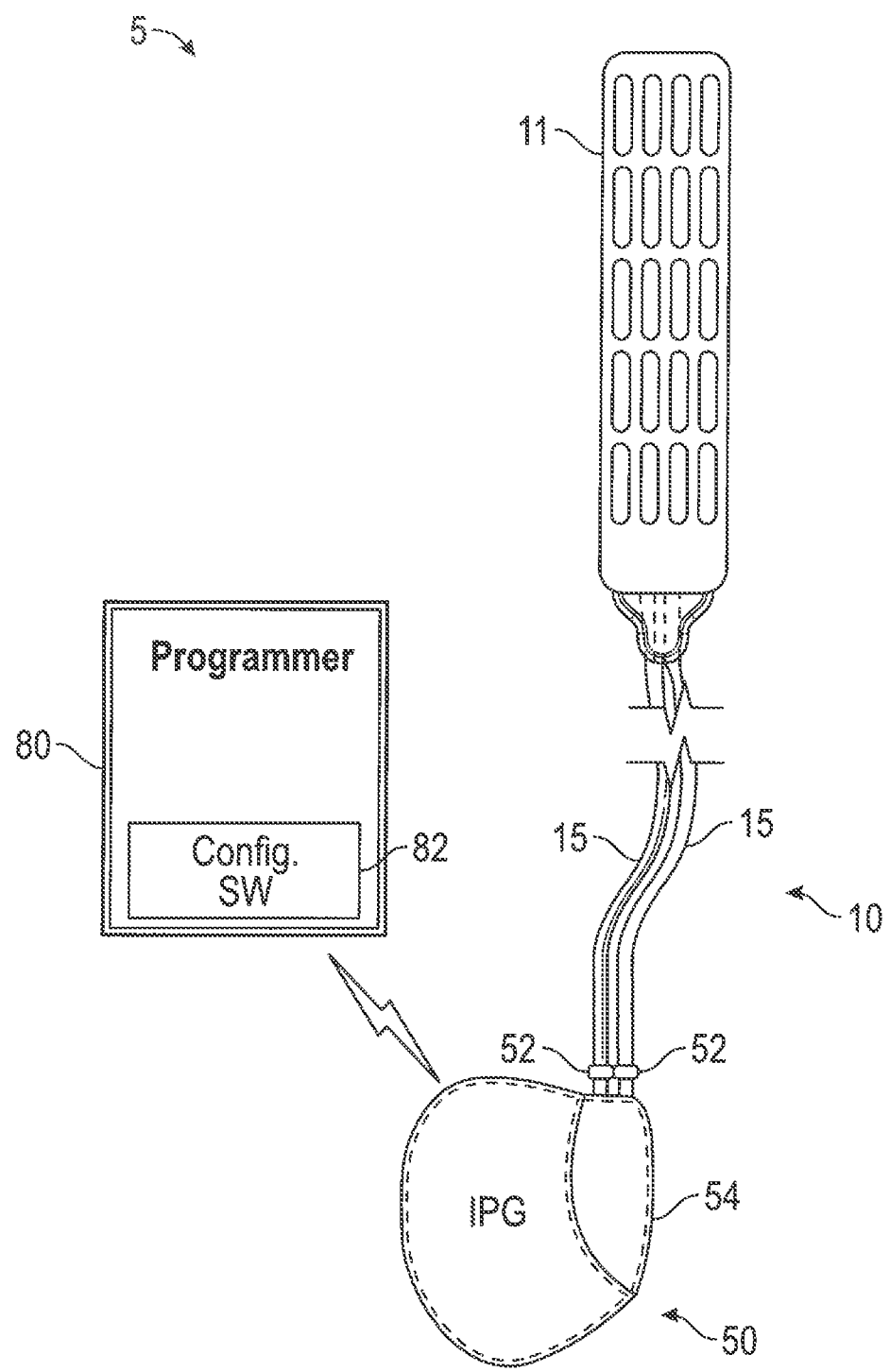
FIG. 2A is a schematic diagram of a neurostimulation system including a paddle lead extending from an implantable pulse generator in communication with a wireless programmer.

FIG. 2A is a schematic diagram of an example neurostimulation system 5 including a paddle lead 10, an implantable pulse generator (IPG) 50, and a programmer 80. The paddle lead 10 extends from the IPG 50. The programmer 80 is in wireless communication with the IPG 50. An example of a commercially available IPG 50 is the Eon™ Rechargeable IPG from Abbott™, although any suitable IPG, such as RF powered devices, could be alternatively employed.

Figure 2B:
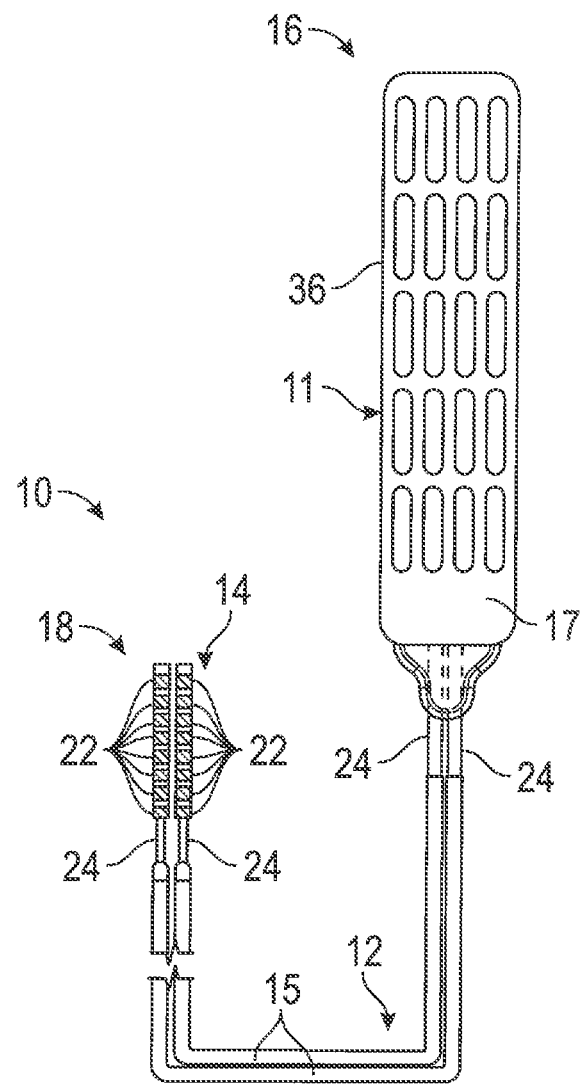
FIG. 2B is a schematic diagram of the paddle lead of FIG. 2A.

FIG. 2B is a schematic diagram of the paddle lead 10 employed in the example system 5 of FIG. 2A. The paddle lead 10 includes a proximal end 14 and a distal end 16. The proximal end 14 includes a connector end or assembly 18 with a plurality of electrically conductive terminals 22. The distal end 16 includes a flexible paddle electrode array 11 that includes a plurality of electrodes 36, which may include one or both of flexible and non-flexible electrodes. The electrodes 36 are arranged within a substantially flat and thin paddle style structure 17. The electrodes 36 are mutually separated by the electrically insulating material of the paddle 17.

A lead body 12 of the lead 10 extends between the flexible paddle electrode array 11 and the connector end 18. Conductors 24, which are embedded within respective insulated sheaths 15 of the lead body 12, electrically connect the electrodes 36 to the terminals 22.

As shown in FIG. 2B, the flexible paddle electrode array 11 may include four columns and five rows of the electrodes 36 arranged in a grid configuration, for a total of twenty electrodes. Alternative numbers of columns and rows may be employed. For example, thirty-two or more electrodes may be distributed into multiple rows and multiple columns. Also, every row need not contain the same number of columns. For example, a number of rows can include a "tri-pole" design having three columns of electrodes while additional rows can include five or more columns of electrodes to enable a greater amount of electrical field resolution.

The multiple columns of electrodes 36 enable lateral control of the applied electrical field to stimulate the exact lateral position of the pertinent nerve fiber(s). Specifically, it may be desirable to selectively stimulate a given dorsal column fiber that is associated with an afflicted region of the patient's body without affecting other regions of the patient's body. The multiple columns of electrodes provide sufficient resolution to relatively finely control the stimulation of one or several specific fibers. Additionally, the multiple columns provide a degree of positional tolerance during the surgical placement of the flexible paddle electrode array 11 within the epidural space, as any one of the columns may be used to stimulate the pertinent nerve fiber(s). Also, if the flexible paddle electrode array 11 is displaced relative to the pertinent nerve fibers subsequent to implantation (e.g., due to lead migration), the stimulation pattern applied by a pulse generator can be shifted between columns to compensate for the displacement.

The multiple rows of electrodes 36 enable multiple pain locations to be treated with a single implanted lead. Specifically, a first row can be used to treat a first pain complaint (e.g., pain in the lower extremities) and a second row can be used to treat a second pain location (e.g., post-laminectomy pain in the back). Furthermore, by separating the first and second rows by one or more "buffer" rows of high-impedance electrodes, the stimulation in the first and second rows may occur on a substantially independent basis. Specifically, anodes in the second row will have relatively minimal effect on the field distribution generated by cathodes in the first row.

The flexible paddle electrode array 11 may be implanted within a patient such that the electrodes 36 are positioned within the cervical or thoracic spinal levels. After implantation, an electrode combination on a first row of electrodes can be determined that is effective for a first pain location with minimal effects on other regions of the body. The first pain location can be addressed by stimulating a specific dorsal column fiber due to the relatively fine electrical field resolution achievable by the multiple columns. Then, another electrode combination on a second row of electrodes can be determined for a second pain location with minimal effects on other regions of the body. The second pain location could be addressed by stimulating another dorsal column fiber as an example. After the determination of the appropriate electrodes for stimulation, a patient's IPG 50 (shown in FIG. 2A), can be programmed to deliver pulses using the first and second rows according to the determined electrode combinations.

The conductors 24 are carried in sheaths 15. In certain paddle leads, each sheath 15 may carry multiple conductors 24. Accordingly, each conductor 24 may be electrically coupled to one of electrodes 36. Multiple electrodes 36 may also be electrically coupled to one conductor 24, thereby allowing paddle configurations in which the number of electrodes 36 exceed the number of available conductors 24.

Other electrode designs may be employed to minimize the number of conductors 24 required to support the electrodes 36. For example, a relatively large number of electrodes (e.g., thirty-two, sixty-four, and greater) could be utilized on the flexible paddle electrode array 11. The electrodes could be coupled to one or several electrical gates (e.g., as deposited on a flex circuit). The electrical gates can be controllably configured to couple each electrode to a conductor carrying cathode pulses, to couple each electrode to an anode termination, or to maintain each electrode at a high impedance state. The electrical gates could be controlled using a main controller, such as a logic circuit, on the flexible paddle electrode array 11 that is coupled to a data line conductor 24. The data line conductor communicates signals from the IPG 50 that identify the desired electrode states, and the main controller responds to the signals by setting the states of the electrical gates as appropriate.

The sheaths 15 and the paddle support structure 17 of the flexible paddle electrode array 11 are preferably formed from a medical grade, substantially inert material, for example, polyurethane, silicone, or the like. Such materials are preferably non-reactive to the environment of the human body, provide a flexible and durable (i.e., fatigue resistant) exterior structure for the components of the paddle lead 10, and insulate adjacent terminals 22 and/or electrodes 36.

The flexible paddle electrode array 11 may be fabricated to possess a substantially flat profile. Alternatively, the flexible paddle electrode array 11 may have an arcuate or bowed profile. A wing structure or other type of stabilization structure may extend along one or both longitudinal sides of the paddle structure 17. Such stabilization structures may be formed for the purpose of retaining the flexible paddle electrode array 11 within the central portion of the epidural space. One or more of the electrodes 36 may be disposed on the stabilization structures.

As can be understood from FIGS. 2A and 2B, the paddle lead 10 is coupled to the IPG 50 by the lead connector assembly 18 of the paddle lead 10 being received in header ports 52 of the IPG 50. Each header port 52 electrically couples the respective terminals 22 to a switch matrix (not shown) within the IPG 50.

The switch matrix selectively connects the pulse generating circuitry (not shown) of the IPG 50 to the terminals 22 of the paddle lead 10, and, hence to electrodes 36. A sealed portion 54 of the IPG 50 contains pulse generating circuitry, communication circuitry, control circuitry, and a battery (not shown) within an enclosure to protect the components after implantation within a patient. The control circuitry may include a microprocessor, one or more application specific integrated circuits (ASICs), and/or any suitable circuitry for controlling the pulse generating circuitry. The control circuitry controls the pulse generating circuitry to apply electrical pulses to the patient via the electrodes 36 of the flexible paddle electrode array 11 according to multiple pulse parameters (e.g., pulse amplitude, pulse width, pulse frequency, etc.). The electrodes 36 are set to function as cathodes or anodes or set to a high-impedance state for a given pulse according to the couplings provided by the switch matrix. The electrode states may be changed between pulses.

When the paddle lead 10 is initially implanted within the patient, a determination of the set(s) of pulse parameters and the electrode configuration(s) that may effectively treat the patient's condition is made. The determination or programming typically occurs through a physician's interaction with configuration software 82 executed on the programmer device 80, as indicated in FIG. 2A. The configuration software 82 steps the physician through a number of parameters and electrode configurations based on a trolling algorithm. In some embodiments, the electrode configurations are stepped through by laterally "steering" the electrical field by moving the anodes and/or cathodes along a row of the paddle. The patient provides feedback to the physician regarding the perceived stimulation that occurs in response to the pulse parameters and electrode configuration(s). The physician may effect changes to the parameters and electrode configuration(s) until optimal pulse parameters and electrode configuration(s) are determined. The final pulse parameters and configurations are stored within the IPG 50 for subsequent use. The pulse parameters and configurations are used by the IPG 50 to control the electrical stimulation provided to the patient via the paddle lead 10. Although single channel IPGs have been described according to some embodiments, multiple current or voltage source IPGs could alternatively be employed.

Figure 3:
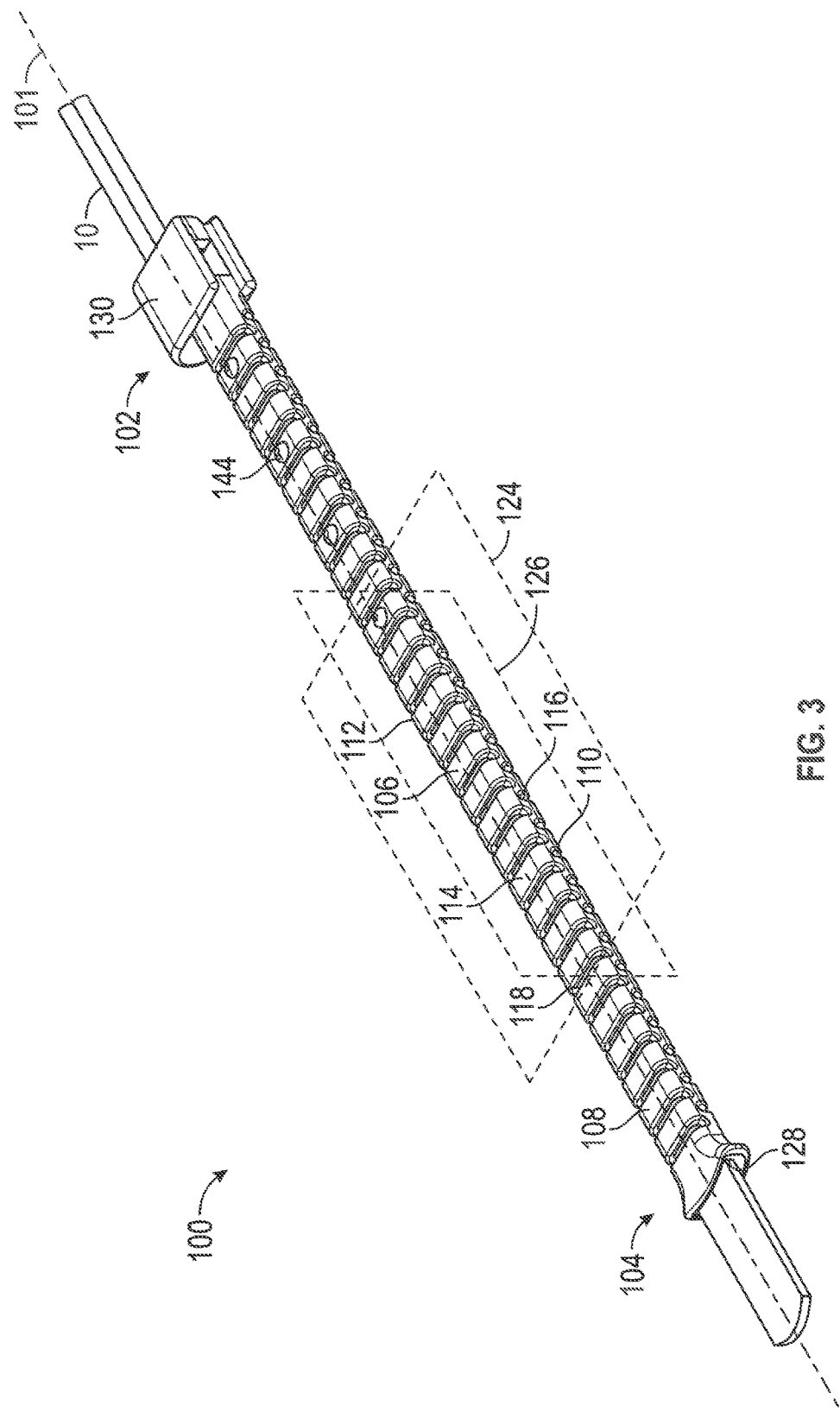
FIG. 3 is an isometric view of a paddle lead delivery tool in a closed configuration with a paddle lead inserted through the paddle lead delivery tool.
Figure 4:
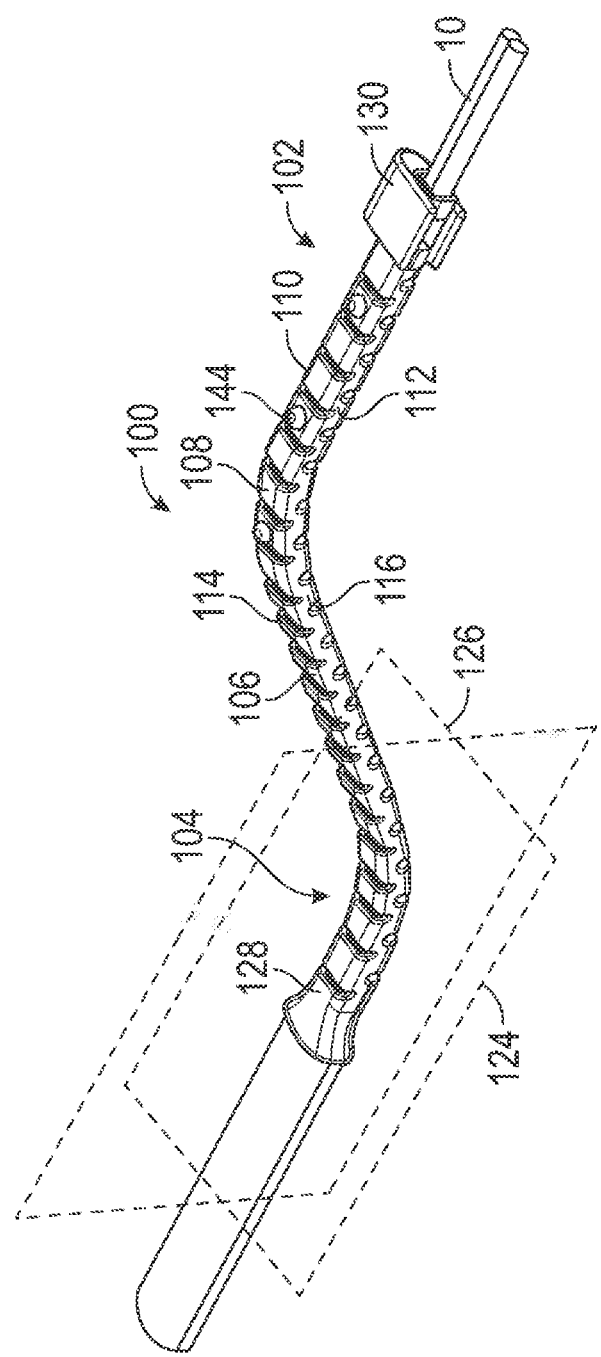
FIG. 4 is a second isometric view of the paddle lead delivery tool of FIG. 3 in a bent configuration.
Figure 5:
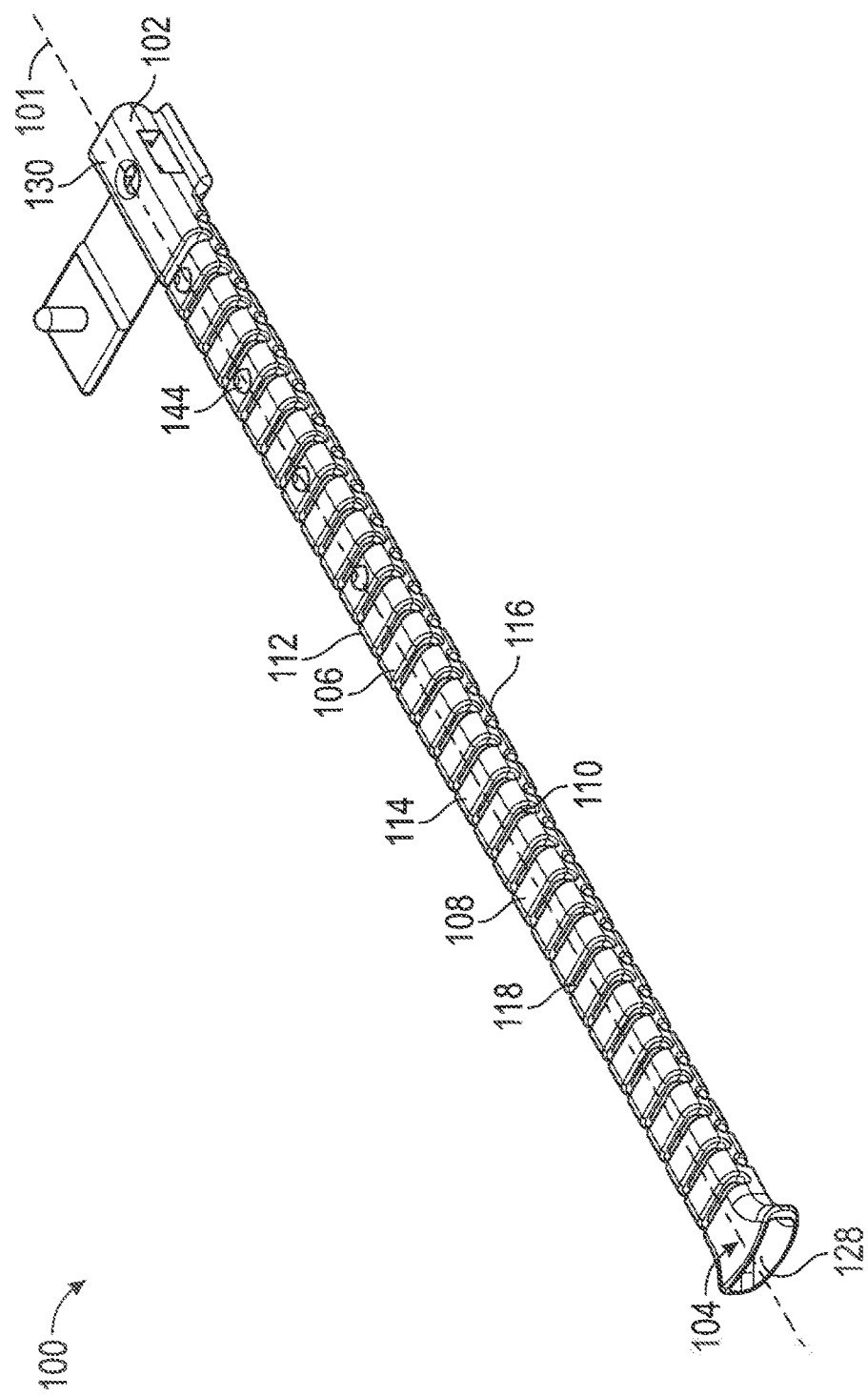
FIG. 5 is an isometric view of the paddle lead delivery tool of FIG. 3 in an open configuration and with the paddle lead omitted.
Figure 6:
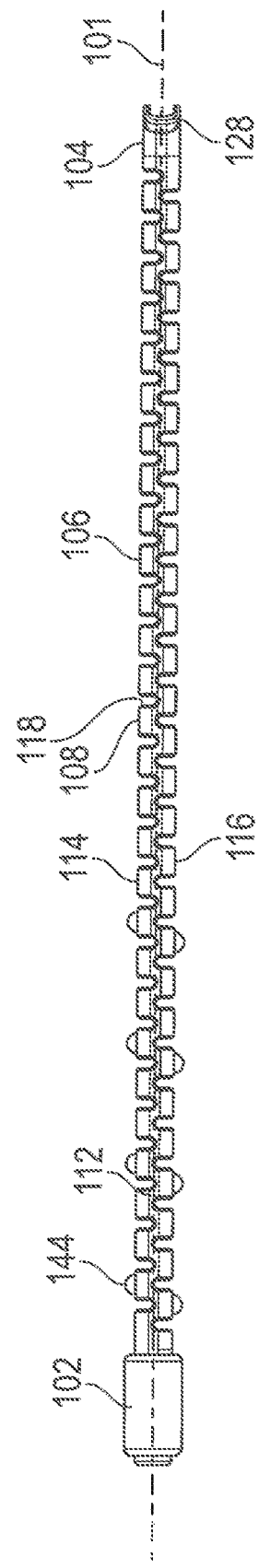
FIG. 6 is a side view of the paddle lead delivery tool of FIG. 3.

FIGS. 3-6 illustrate a first lead delivery tool in accordance with the present disclosure. FIG. 3 is an isometric view of a paddle lead delivery tool 100 in accordance with this disclosure. More specifically, FIG. 3 illustrates the paddle lead delivery tool 100 in a closed configuration with a paddle lead 10 inserted therein, such as would be the case when preparing to implant the paddle lead 10 in a patient. FIG. 4 is a second isometric view of the lead delivery tool 100 in a bent configuration. FIG. 5 is a third isometric view of the lead delivery tool 100 in an open configuration and with the paddle lead 10 removed. FIG. 6 is a plan view of the lead delivery tool 100.

With reference to FIG. 3, the paddle lead delivery tool 100 includes a proximal tool end 102, a distal tool end 104 opposite the proximal tool end 102, and a tool body 106 extending between the proximal tool end 102 and the distal tool end 104 and defining a longitudinal axis 101. The tool body 106 is generally structured such that the tool body 106 resists each of compression along the longitudinal axis 101 of the tool body 106 and bending of the tool body 106 in a lateral direction (e.g., the ML direction) while still allowing bending in a direction perpendicular to the lateral direction (e.g., the AP direction).

The lead delivery tool 100 and its various components may be made from a variety of materials such as, for example, Polypropylene (PP), Polyethylene (PE), Acrylonitrile Butadiene Styrene (ABS), Nitinol or similar alloys, etc. The lead delivery tool 100 may be disposable or capable of being sterilized and reused. Further, in certain implementations, the delivery tool 100 may have a unitary structure and may be formed using various known processes including, without limitation, one or more of injection molding, machining, and three-dimensional printing. Alternatively, the delivery tool 100 may be comprised of multiple segments that are joined to form a unitary structure. Such joining may be achieved by one or more of mechanical fasteners (including mechanical fasteners integrated directly into the components), adhesives, chemical bonding, welding, or any suitable method of joining the components.

The paddle lead delivery tool 102 of FIGS. 3-6 includes a plurality of structural members, such as lateral member 108, extending across the tool body 106 and forming a pair of longitudinal struts 110, 112 extending along the length of the tool body 106. More specifically, the longitudinal struts 110, 112 are formed by the interaction of the lateral members 108 extending across a top 114 of the tool body 106 with the lateral member 108 extending across a bottom 116 of the tool body 106.

In the implementation illustrated in FIGS. 3-6, the lateral members 108 are distributed along the longitudinal struts 110, 112 such that gaps 118 or similar slot structures are defined between adjacent lateral members 108. In the implementation illustrated in FIGS. 3-6, for example, the gaps 118 between adjacent lateral members 108 extend through the tool body 106 and into an internal space defined by the tool body 106.

During use, the longitudinal struts 110, 112 resist bending of the tool body 106 along a first plane 124 (e.g., the ML plane) and planes parallel thereto. In contrast, the gaps 118 reduce resistance to bending of the tool body in a second plane 126 perpendicular to the ML plane (e.g., the AP plane). More specifically, the gaps 118 reduce resistance to bending in the second plane 126. Bending in the second plane 126 is generally limited by the gaps 118 defined between adjacent lateral members 108, which close as the tool body 106 is deformed during bending. Accordingly, when adjacent lateral members 108 contact each other, further bending along the second plane 126 at the location of the contacting lateral members 108 is resisted. The directional flexibility of the tool body 106 enables the tool body 106 to be bent into s-shaped or similar multibend configurations. One such configuration is illustrated in FIG. 4.

The width, longitudinal spacing, and height of the lateral members 108 may be modified to change the limits to which the tool body 106 is permitted to bend and the general resistance to bending in the second plane 126. For example, increasing the longitudinal spacing between adjacent lateral members 108 in a region of the tool body 106 generally increases the degree and ease with which the tool body 106 may be bent in the region. In certain implementations, the spacing, size, and arrangement of the lateral members 108 along the length of the tool body 106.

Figure 7A:
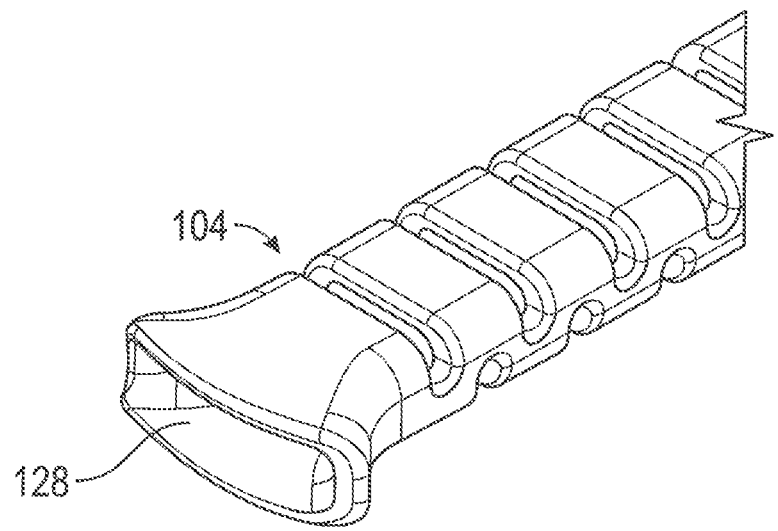
FIG. 7A is an isometric view of a distal end of the paddle lead delivery tool of FIG. 3.
Figure 7B:
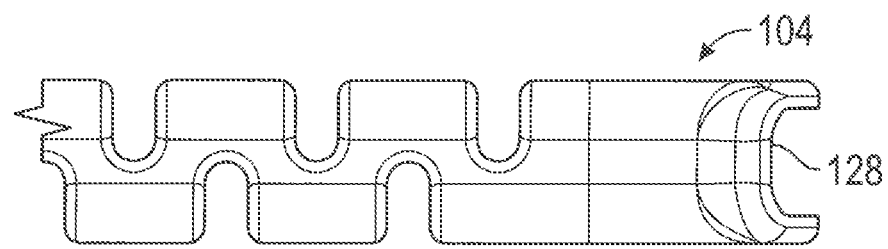
FIG. 7B is a side view of the distal end of FIG. 7A.
Figure 7C:
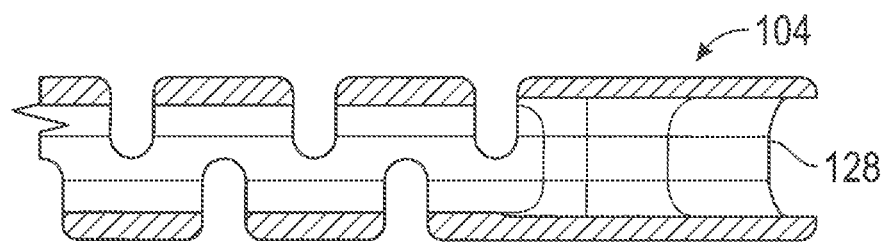
FIG. 7C is a cross-sectional side view of the distal end of FIG. 7A.

The distal end 104 of the lead delivery tool 100 may include a paddle retention feature 128 adapted to receive the paddle electrode array 11 of the paddle lead 10 and to prevent passage of the paddle electrode array 11 into the tool body 106. In certain implementations, the paddle retention feature 128 may include a clip, slot, or similar structure adapted to mate with and positively retain a portion the paddle lead array 11, for example by an interference or press fit, within the retention feature 128. FIGS. 7A-7C are isometric, side, and cross-sectional side views, respectively, of the paddle retention feature 128 of the lead delivery tool 100. As illustrated, the paddle retention feature 128 may be a tapered or bell-like structure adapted to receive the paddle electrode array 11 when the paddle lead 10 is threaded through the tool body 106. The tapered surface providing a stop that abuts the paddle electrode array 11 and prevents the paddle electrode array 11 from entering the tool body 106.

Referring back to FIGS. 3-6, the proximal end 102 of the lead delivery tool 100 may include a lead retention feature 130 adapted to fix the position of the paddle lead 10 and, more specifically, the lead body 12 relative to the tool body 106. To do so, the lead retention feature 130 may include structures capable of being used to selectively engage a portion of the lead body 12. Accordingly, during use the lead retention feature 130 may be in a disengaged configuration when the paddle lead 10 is inserted into the lead delivery tool 100 in preparation for implantation. Once the paddle lead 10 is inserted, the lead retention feature 130 may be engaged to effectively lock the position of the paddle lead 10 within the lead delivery tool 100 during the course of insertion of the paddle electrode array 11 into the epidural space of the patient. After the paddle electrode array 11 is positioned within the epidural space, the lead retention feature 130 may be disengaged, thereby allowing the led delivery tool 100 to be slid away from the paddle electrode array 11 and off of the paddle lead 10.

Figure 8A:
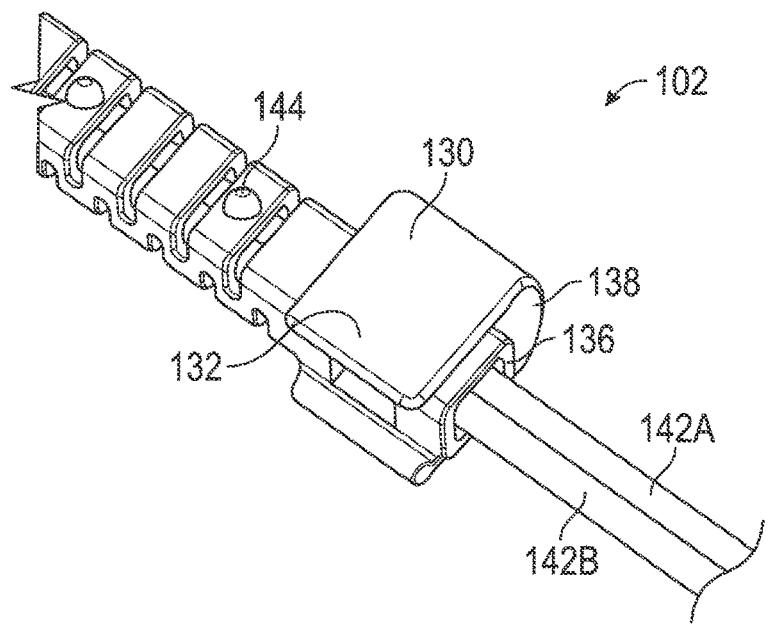
FIG. 8A is an isometric view of a proximal end of the paddle lead delivery tool of FIG. 3 in a closed configuration.
Figure 8B:
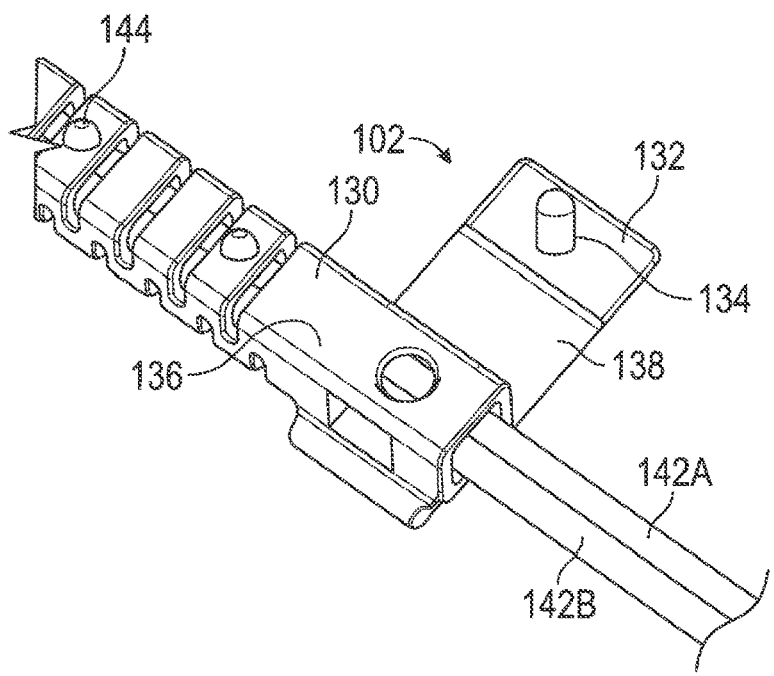
FIG. 8B is an isometric view of the proximal end of FIG. 8A in an open configuration.

FIGS. 8A-8B illustrate the lead retention feature 130 of the lead delivery tool 100 in a closed (engaged) configuration and an open (disengaged) configuration, respectively. The lead retention feature 130 may be used with paddle leads having a dual lead body configuration. As shown in FIG. 8B, the lead retention feature 130 includes an upper tab 132 from which a protrusion 134 extends. The upper tab 132 is coupled a lead retention feature body 136 by a living hinge 138 that allows the upper tab 132 to overlap the lead retention feature body 136 such that the protrusion 134 extends through a hole 140 defined in the lead retention feature body 136. When a pair of paddle lead bodies, such as paddle lead bodies 142A and 142B, are inserted into the lead retention feature body 136 insertion of the protrusion 134 into the lead retention feature body 136 positions the protrusion 134 between the paddle lead bodies 142A, 142B. When the protrusion 134 is inserted between the paddle lead bodies 142A, 142B, press or interference fits between the paddle leads 142A, 142B and each of the protrusion 134 and the lead retention feature body 136 fix the position of the paddle lead 10 within the lead delivery tool 100.

Referring back to FIGS. 3-6, the tool body 106 may include gripping features 144 disposed along a portion of its length. For example, tool body 106 includes a plurality of gripping features 144 in the form of hemispherical knobs protruding from proximal portions of each of the top 114 and the bottom 116 of the tool body 106. In other implementations, the gripping features 144 may include, without limitation, one or more of indentations, rough surfaces, and protrusions other than hemispherical protrusions.

Figure 9:
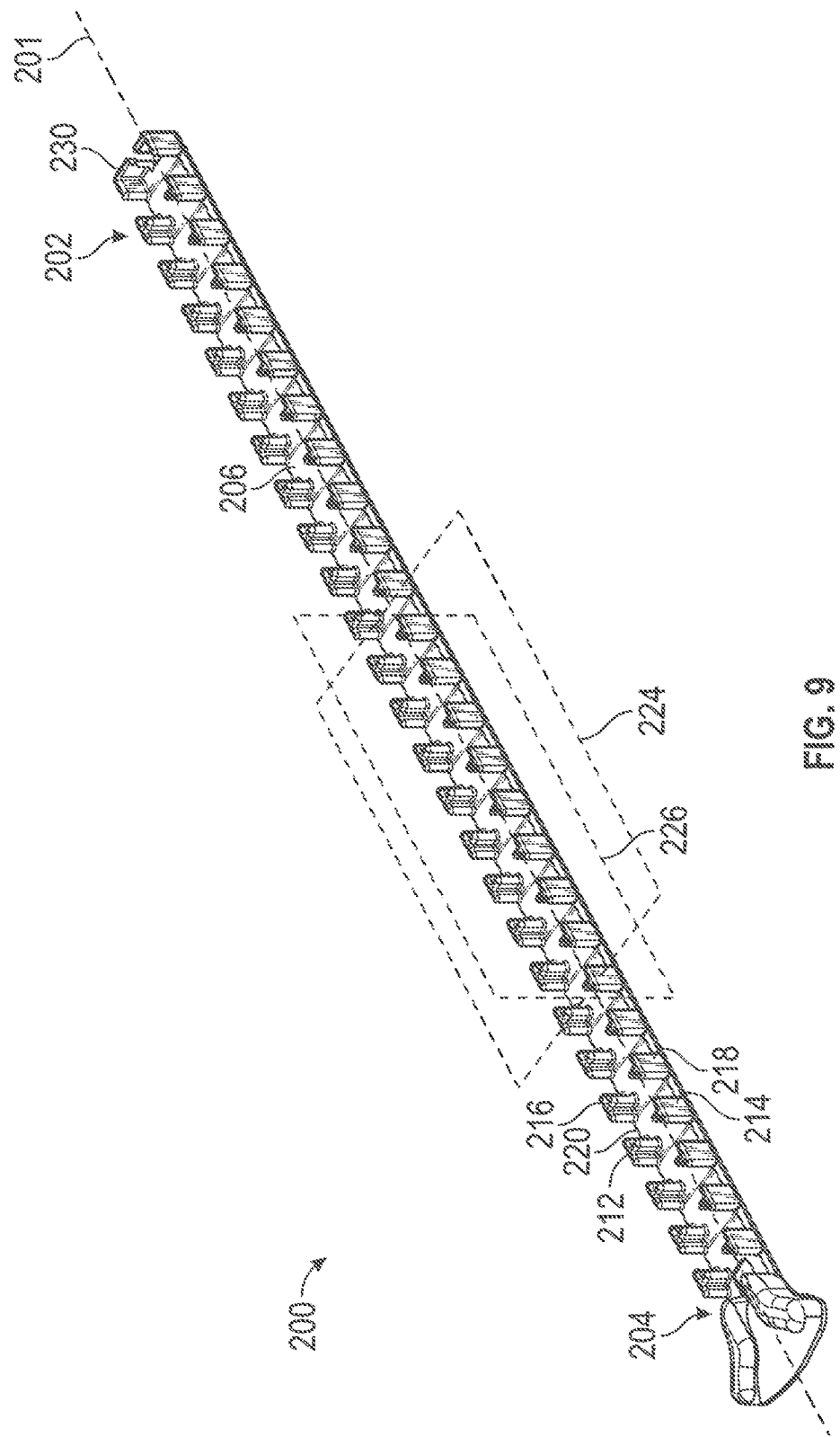
FIG. 9 is an isometric view of a second paddle lead delivery tool.

FIG. 9 is an isometric view of a second lead delivery tool 200 according in accordance with this disclosure. The paddle lead delivery tool 200 includes a proximal tool end 202, a distal tool end 204 opposite the proximal tool end 202, and a tool body 206 extending between the proximal tool end 202 and the distal tool end 204 and defining a longitudinal axis 201. Similar to the lead delivery tool 100 of FIGS. 3-6, the tool body 206 is generally structured such that the tool body 206 resists each of compression of the tool body 206 along the longitudinal axis 201 and bending of the tool body 206 in a lateral direction (e.g., along the ML plane) while still allowing bending in a direction perpendicular to lateral (e.g., along the AP plane).

In certain implementations, the tool body 206 may include a longitudinal primary structure 210 from which structural members, such as structural members 212-218 protrude. The longitudinally extending structure 210 shown in FIG. 9, for example, is a solid strip 210 from which t-shaped structural members 212-218 extend. The structural members 212-218 are distributed along the strip 210 in inwardly facing pairs that are offset such that slots or gaps 220 are defined between adjacent pairs of the structural members. For example, structural members 212 and 214 form a first pair and structural members 216 and 218 form a second pair offset from the first pair, such that the first and second pairs of structural members define a slot 220 therebetween. Accordingly, the tool body 206 resists both bending along the ML plane 224 and compression along the longitudinal axis 201 while permitting bending along the AP plane 226. Bending along the AP plane 226 is limited, at least in part, by the structural members. More specifically, the tool body 206 may be bent along the AP plane to an extent where adjacent structural members in the region of the bend abut each other and resist additional bending.

Figure 10:
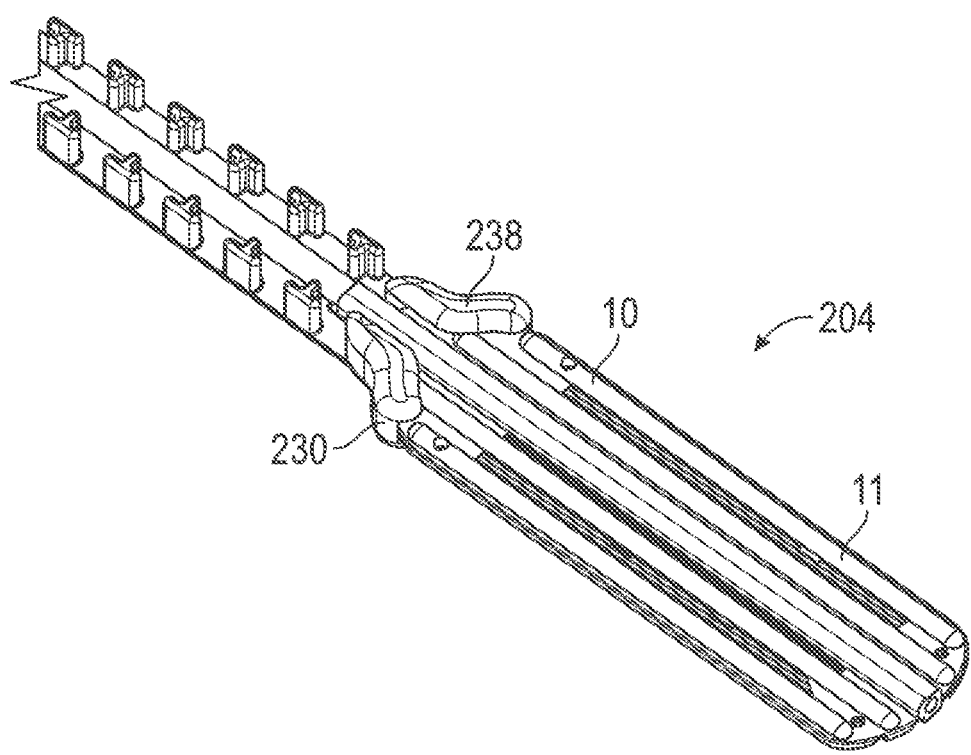
FIG. 10 is an isometric view of a distal end of the paddle lead delivery tool of FIG. 9 including a paddle lead.

FIG. 10 is an isometric view of the distal end 204 of the lead delivery tool 200, which includes a paddle retention feature 228 adapted to receive the paddle electrode array 11 of the paddle lead 10. The paddle retention feature 228 may be formed of a flexible material and define a paddle retention slot 230 adapted to receive a proximal end of the paddle electrode array 11. Also, the paddle retention slot 230 may be adapted such that when the paddle electrode array 11 is inserted into the paddle retention slot 230, an interference fit is formed between the paddle electrode array 11 and the paddle retention feature 228, thereby causing the paddle electrode array 11 to be positively retained by the paddle retention feature 228.

Although the slots 220 between adjacent pairs of structural members is illustrated in FIG. 9 as being substantially rectangular and extending fully downward to the strip 210, in other implementations, other slot shapes may be used. Accordingly, FIGS. 11A-11C are side views of tool bodies in accordance with the present disclosure that may be used with the lead delivery tool 200 and are intended to illustrate various arrangements of structural members and intermediate slots.

FIG. 11A is a plan view of the tool body 206 of the lead delivery tool 200 of FIG. 9. The tool body 206 is formed of the longitudinal strip 210 from which t-shaped structural members extend such that slots are defined between adjacent structural members. For example, as illustrated in FIG. 11A, structural members 212 and 216 define a slot 220 therebetween.

FIG. 11B is a plan view of an alternative tool body 306 such as may be used in the lead delivery tool 200 of FIG. 9. The tool body 306 includes a longitudinal strip 310 from which structural members, such as structural members 312 and 316, extend. The structural members of FIG. 11B omit the optional t-shape and, instead, are substantially rectangular in cross-section. Slots, such as slot 320, are defined between adjacent structural members. In contrast to the implementation illustrated in FIG. 11A, the slot 320 is a lateral rib extending across the width of the longitudinal strip 310. In certain implementations a groove 322 may be defined in each such rib to retain and guide a lead body of a paddle lead, such as the lead body 15 illustrated in FIG. 2B.

FIG. 11C is a plan view of another alternative tool body 406 such as may be used in the lead delivery tool 200 of FIG. 9. The tool body 406 includes a longitudinal strip 410 from which structural members, such as structural members 412 and 416, extend. Slots, such as slot 420, are defined between adjacent structural members by a thin wall or web 422 extending between the adjacent structural members. Although illustrated as being curved, the web 422 extending between adjacent structural members may be flat, stepped, or any other suitable shape such that the web 422 extends below the adjacent structural members 412, 416.

Similar to the lateral members of the delivery tool 100 of FIG. 3, the height, width, spacing, and general arrangement of the structural members of the implementations illustrated in FIGS. 9 and 11A-11C may be varied to adjust the bending properties of the corresponding tool bodies.

Figure 12A:
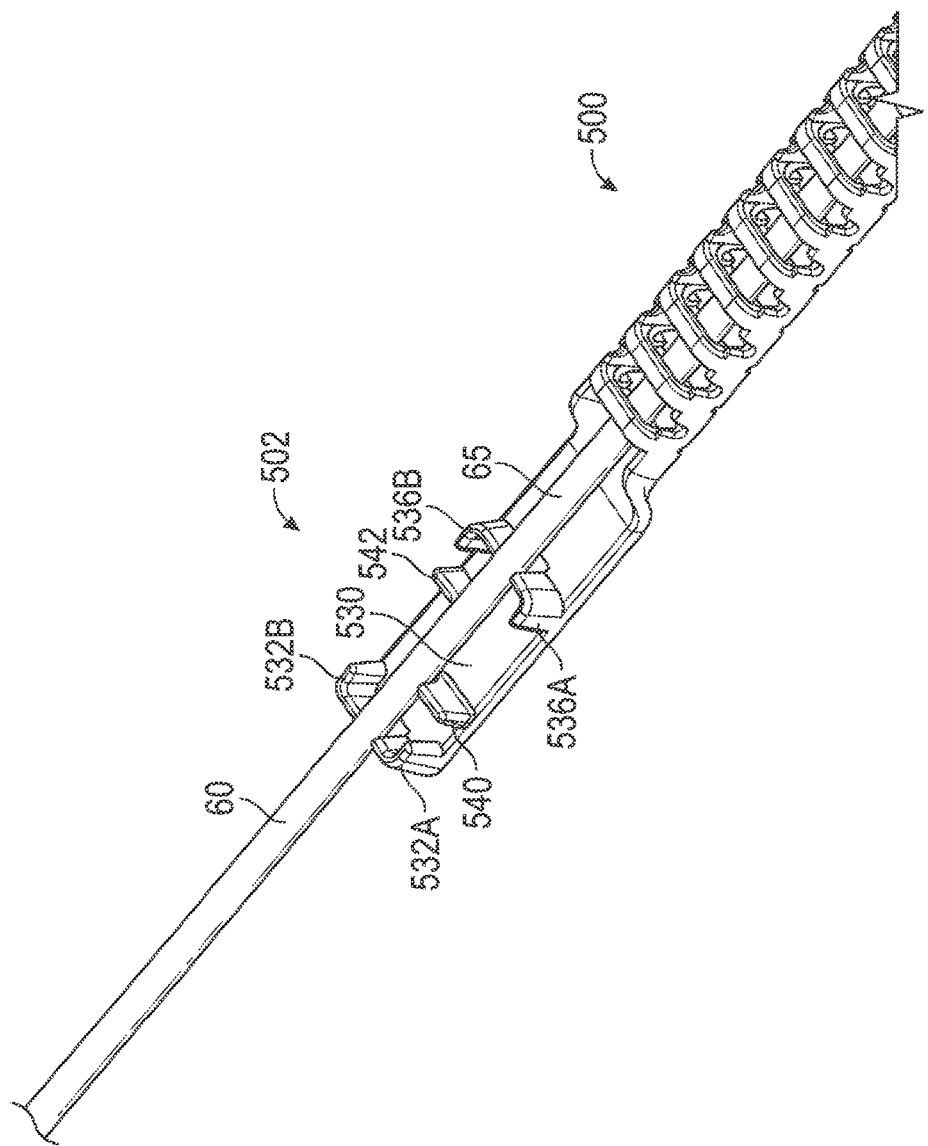
FIG. 12A is an isometric view of a proximal end of a third paddle lead delivery tool including a paddle lead.
Figure 12B:
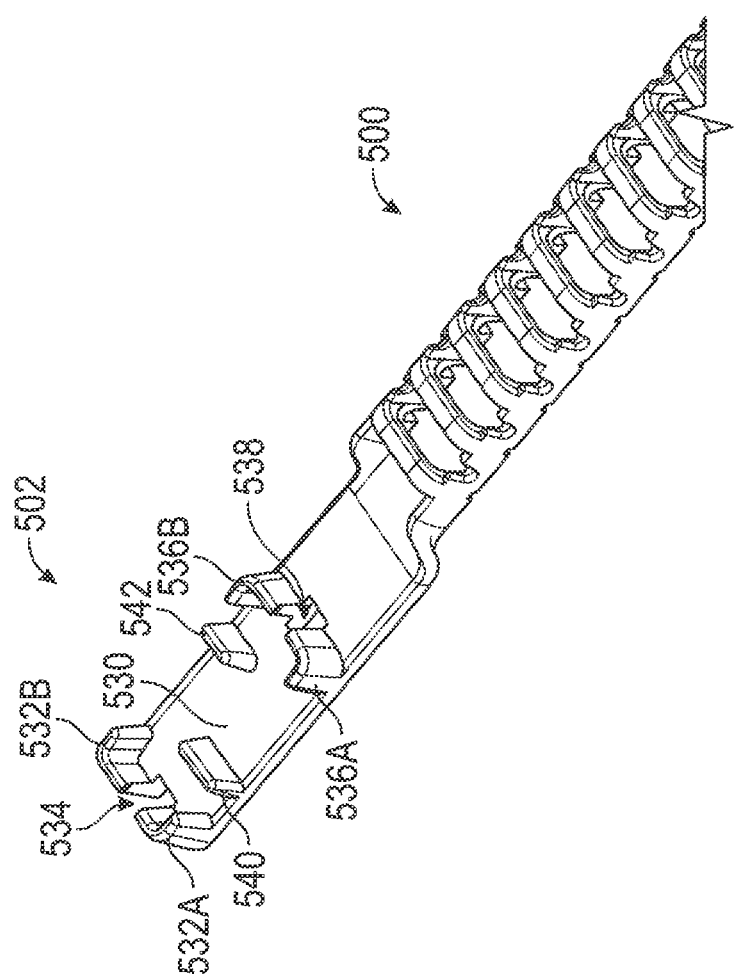
FIG. 12B is an isometric views of the proximal end of FIG. 12A with the paddle lead omitted.

FIGS. 12A and 12B are isometric views of a proximal end 502 of another lead delivery tool 500 in accordance with this disclosure. The proximal end 502 includes a lead retention feature 530 that, as shown in FIG. 12A, is adapted to receive a portion of a lead body 65 of a paddle lead 60. The lead retention feature 530 includes a pair of inlet walls 532A, 532B defining a lead inlet 534 (shown in FIG. 12B), a pair of outlet walls 536A, 536B defining a lead outlet 538 (shown in FIG. 12B) and intermediate walls 540, 542 that define a tortuous/serpentine path between the lead inlet 534 and the lead outlet 538. The arrangement of the walls of the lead retention feature 530 is such that when the lead body 65 of the paddle lead 60 is inserted into the lead retention feature 530 and made to follow the serpentine path between the lead inlet 534 and the lead outlet 538, sufficient force is exerted by the lead body 65 onto the walls to retain the paddle lead 60 relative to the lead delivery tool 500. Although illustrated in FIGS. 12A-12B as being adapted to receive a paddle lead 60 including a single lead body 65, the lead retention feature 530 may be adapted to retain more than one lead body to accommodate paddle leads having multiple lead bodies. For example, in certain implementations, the serpentine path defined between the lead inlet 534 and the lead outlet 538 may be widened to accommodate multiple paddle leads or additional intermediate walls may be introduced to define multiple serpentine paths, each serpentine path adapted to retain a subset of the lead bodies.

Figure 13A:
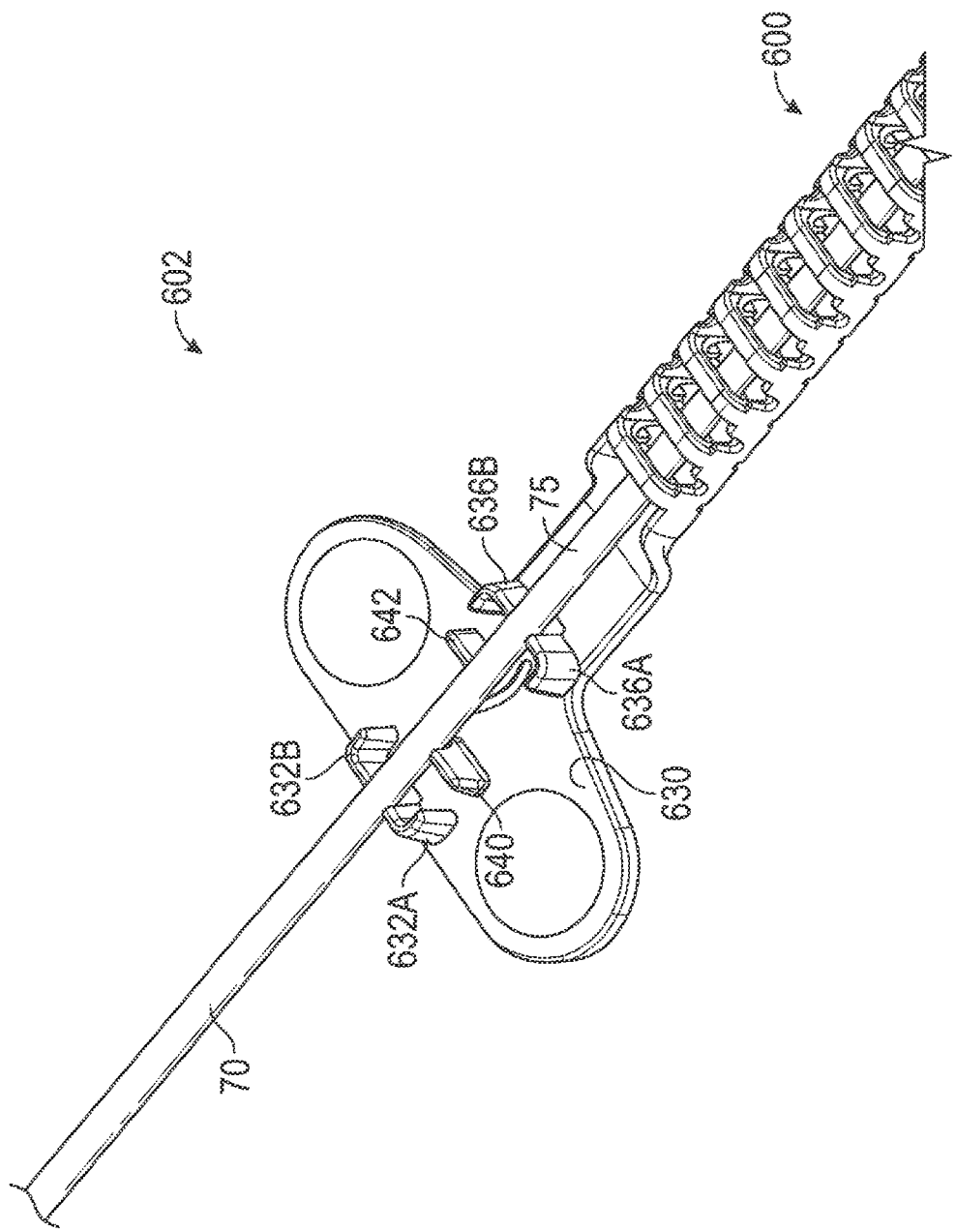
FIG. 13A is an isometric view of a proximal end of a fourth paddle lead delivery tool including a paddle lead.
Figure 13B:
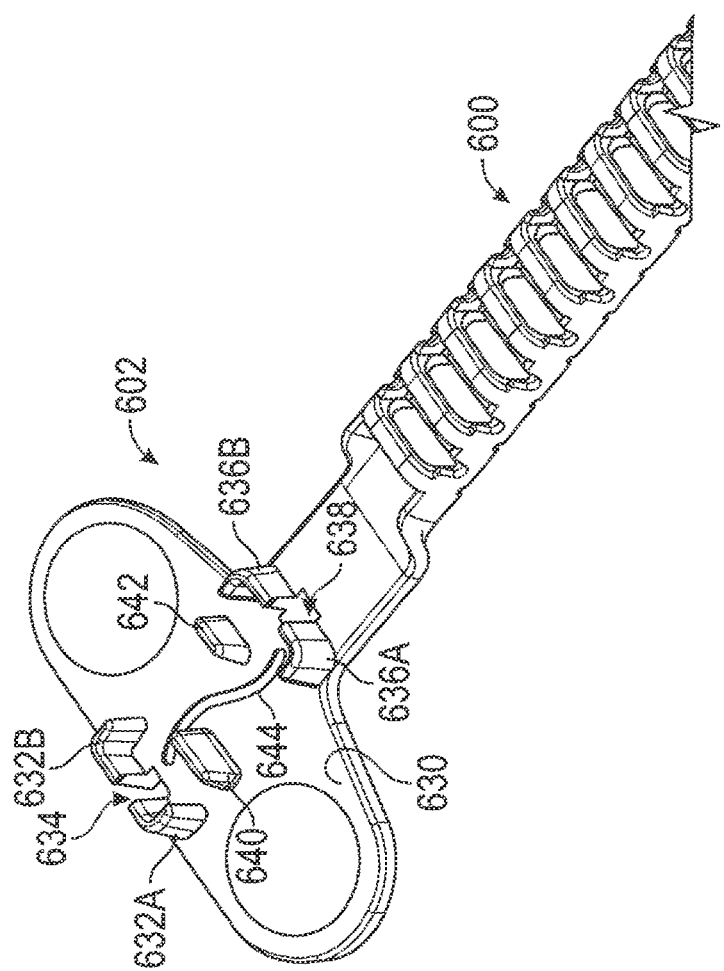
FIG. 13B is an isometric views of the proximal end of FIG. 13A with the paddle lead omitted.

FIGS. 13A and 13B are isometric views of a proximal end 602 of yet another lead delivery tool 600 in accordance with this disclosure. The proximal end 602 includes a lead retention feature 630 that, as shown in FIG. 13A, is adapted to receive a portion of a lead body 75 of a paddle lead 70. Similar to the lead retention feature 520 of FIGS. 13A-13B, the lead retention feature 630 includes a lead inlet 634, a lead outlet 638 (each shown in FIG. 13B) and intermediate walls 640, 642 that define a serpentine path between the lead inlet 634 and the lead outlet 638 along which the lead body 75 is retained. As shown in FIG. 13B, the lead retention feature 630 further includes a groove 644 to guide the lead body 75 and a handle 646 to facilitate gripping of the lead delivery tool 600 during implantation of the paddle lead 70.

Figure 14A:
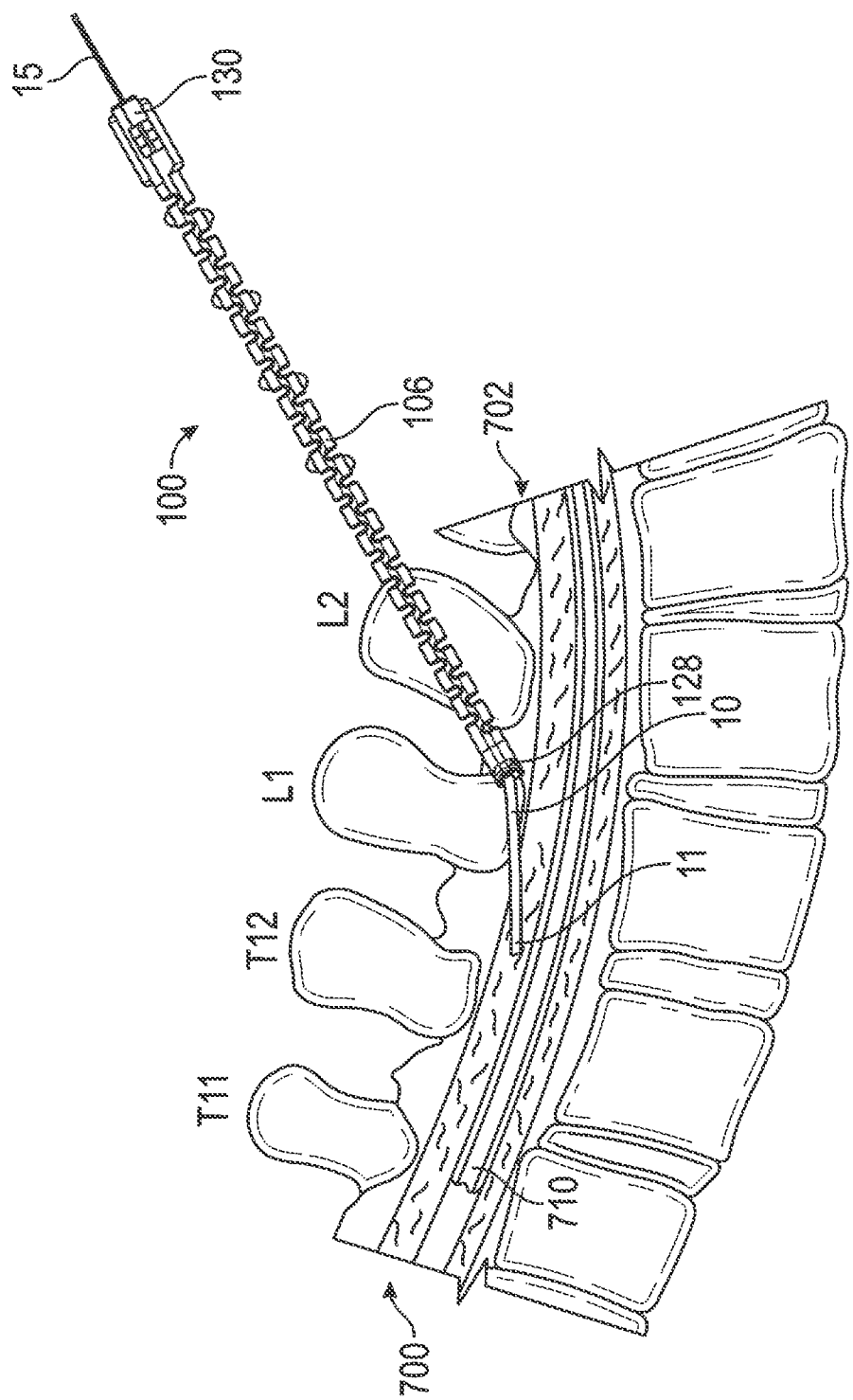
FIG. 14A shows an example paddle lead delivery tool inserted into epidural space of a patient.
Figure 14B:
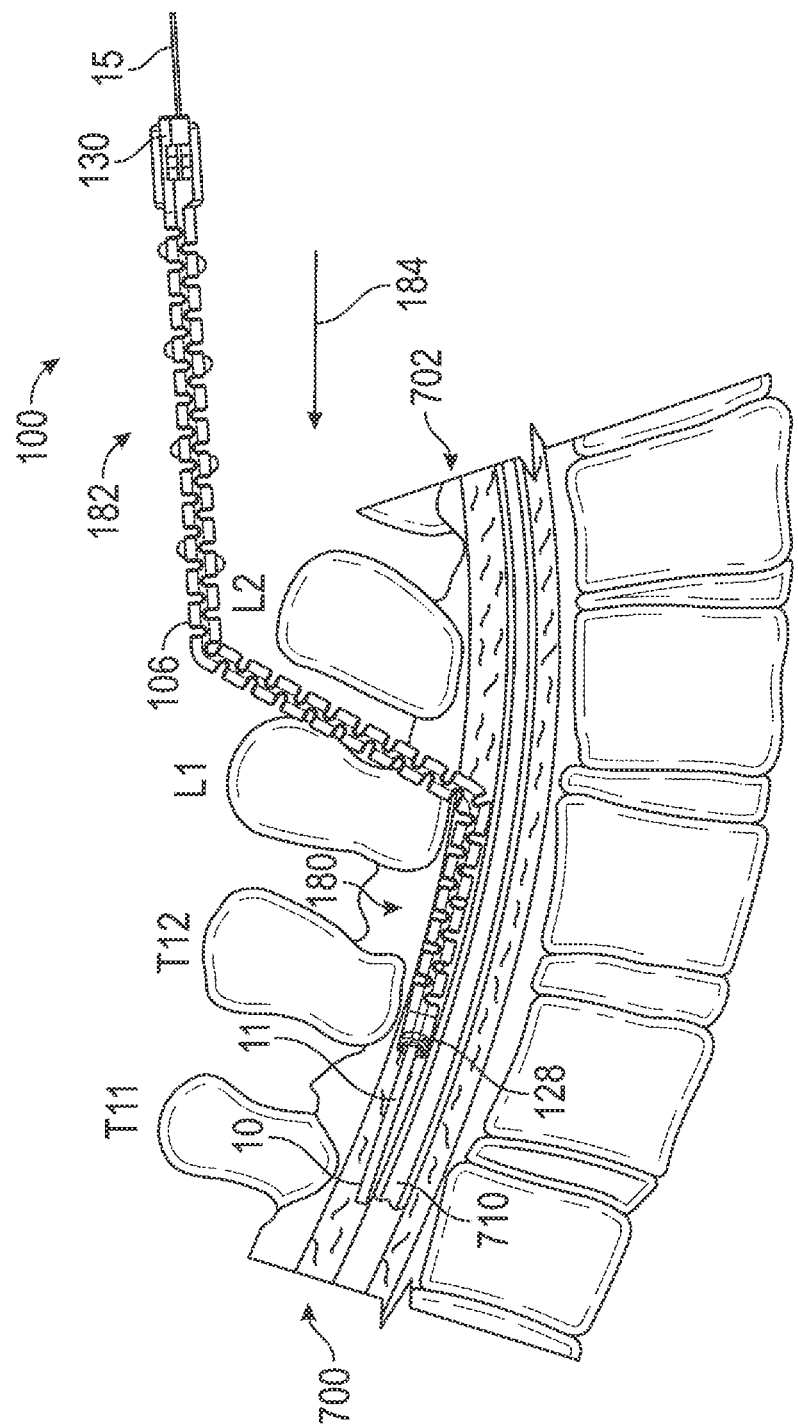
FIG. 14B illustrates the paddle lead delivery tool of FIG. 14A during placement of the paddle lead within the epidural space of the patient.
Figure 14C:
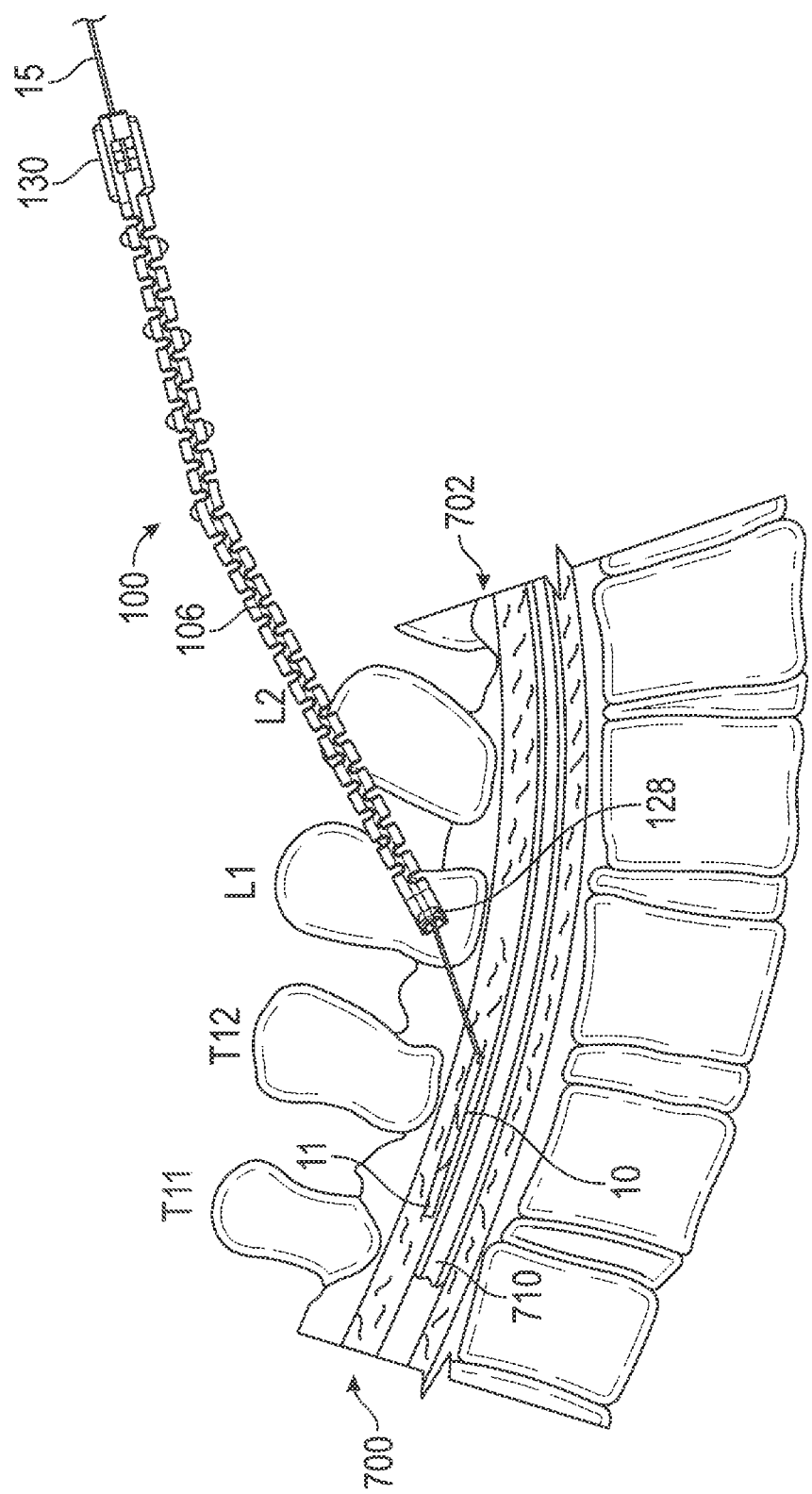
FIG. 14C illustrates removal of the paddle lead delivery tool of FIG. 14A after placement of the paddle lead within the epidural space of the patient.

FIGS. 14A-14C illustrate an implantation procedure of a paddle lead using the lead delivery tool 100 of FIGS. 3-6. In one implementation, a target location in the epidural space 700 of a patient is chosen for positioning a paddle lead 10 to deliver SCS treatment. In the example procedure illustrated in FIGS. 14A-14C, the paddle lead 10 is to be implanted within the epidural space 700 adjacent the T11 and T12 vertebrae and the spinal cord 710. The target location may be selected, for example, using fluoroscopy. To improve access to the selected region of the epidural space 700 and facilitate insertion of the paddle lead 10, a laminectomy may be performed prior to implantation of the paddle lead 10. Doing so removes the lamina of vertebrae near the implantation region and improves access to the epidural space 700. For example, in the procedure illustrated in FIGS. 14A-14C, a full or partial laminectomy may be performed on the L1 or L2 vertebrae to improve access to the epidural space 700.

Prior to implantation, the paddle lead 10 is inserted into the lead delivery tool 100. More specifically, while the lead delivery tool 100 is in an open configuration (i.e., when the lead retention feature 130 is open), the lead body or bodies 15 of the paddle lead are inserted into the distal end 104 of the lead delivery tool 100, threaded through the lead body 106, and out of the proximal end of the lead retention feature 130 such that the paddle electrode array 11 abuts or is otherwise received by the paddle retention feature 128 of the lead delivery tool 100. The lead retention feature 128 is then engaged to retain the paddle lead relative to the lead delivery tool 100. In implementations in which a lead delivery tool including a serpentine path-type lead retention feature (such as the lead retention feature 530 illustrated in FIGS. 12A-12B) is implemented, retention of the paddle lead is instead accomplished by pressing the lead body into the lead retention feature 530 such that it is made to follow the serpentine path defined by the lead retention feature 530.

As illustrated in FIG. 14A, the lead delivery tool 100 and the paddle lead 10 retained by the lead delivery tool 100 are guided through subcutaneous tissue and the ligamentum flavum 702 and into the epidural space 700 along the spinal cord 704. Initial insertion of the paddle lead 10 may be accomplished with the lead delivery tool 100 in a substantially linear orientation owing, in part, to the flexibility of the paddle electrode array 11.

As illustrated in FIG. 14B, the lead delivery tool 100 may then be bent in multiple locations to facilitate positioning of the paddle lead 10 in its final location (i.e., within the epidural space 700, anterior the T11 and T12 vertebrae). As previously discussed, the tool body 106 of the lead delivery tool 100 is adapted to resist bending along the ML plane, which, during use, generally corresponds to the coronal plane of the patient. The tool body 106 is further adapted to allow bending along the AP plane, which generally corresponds to the coronal plane of the patient, to an extent that is limited by the arrangement of lateral members 108 and intermediate gaps 118 of the lead delivery tool 100.

As previously illustrated in FIG. 4, the flexibility of the lead delivery tool 100 along the AP plane allows the lead delivery tool 100 to be bent substantially into a double-curve or s-shape. In the context of an implantation, the flexibility of the lead delivery tool 100 may be used to facilitate placement of the paddle lead 10 within the epidural space 700. For example, FIG. 14B illustrates an arrangement in which a first, distal portion 180 of the lead delivery tool 100 is disposed within the epidural space 700 and a second, proximal portion 182 of the lead delivery tool 100 is disposed external the patient, posterior the first portion 180 such that the second portion 182 is accessible during the implantation procedure. The flexibility of the lead delivery tool 100 enables the relative angle between the first portion 180 and the second portion 182 to be minimized such that a longitudinal force 184 applied to the second portion 182 is substantially translated to the first portion 180, thereby causing the first portion 180 and the paddle lead 10 retained therein to move into the epidural space 700. Such movement may cause the bends in the lead delivery tool 100 to shift.

Once the paddle lead 10 is positioned in its final location, the lead delivery tool 100 may be decoupled from the paddle lead and removed. As illustrated in FIG. 14C, removal of the lead delivery tool 100 may generally involve the steps of disengaging the lead retention feature 130 and then sliding the lead delivery tool 100 off a proximal end of the paddle lead 10. In other implementations, disengagement of the paddle retention feature may include removing a lead body of the paddle lead from a serpentine path defined by the paddle retention feature.

In certain implementations, such as the implementation illustrated in FIG. 10, the paddle electrode array may also need to be disengaged from a paddle retention feature disposed at the distal 104 end of the lead delivery tool 100. Such disengagement may occur simply by pulling the lead delivery tool 100 due to friction between the paddle electrode array 11 and surfaces of the epidural space 700. Alternatively, disengagement of the paddle electrode array 11 from the paddle retention feature may be affected by pulling the lead delivery tool 100 away from the paddle electrode array 11 while simultaneously holding or applying a force in the opposite direction on the paddle lead 10.

Various other modifications and additions can be made to the exemplary implementations discussed without departing from the spirit and scope of the presently disclosed technology. For example, while the embodiments described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. A delivery tool for use in implanting a paddle lead, the delivery tool having a proximal tool end and a distal tool end opposite the proximal end and the paddle lead including a paddle electrode array disposed at a distal end of a paddle lead body, the delivery tool comprising:
    a tool body extending between the proximal tool end and the distal tool end and adapted to receive a portion of the paddle lead body, the tool body comprising:
        a longitudinal member extending along the tool body; and
        a plurality of structural members extending from the longitudinal member and distributed along the longitudinal member such that gaps are defined between longitudinally adjacent structural members.

2. The delivery tool of claim 1, wherein the longitudinal member and the plurality of structural members are adapted to have a first resistance to bending of the tool body in a first plane and to have a second resistance, less than the first resistance, to bending along a second plane perpendicular to the first plane.

3. The delivery tool of claim 2, wherein the longitudinal member is a first longitudinal member extending along a first lateral side of the tool body and the tool body comprises a second longitudinal member extending along a second lateral side of the tool body opposite the first lateral side, each of the plurality of structural members extending laterally from the first longitudinal member to the second longitudinal member.

4. The delivery tool of claim 3, wherein a first set of the structural members extends from the first longitudinal member to the second longitudinal member across a first side of the tool body and a second set of the structural members extends from the first longitudinal member to the second longitudinal member across a second side of the tool body opposite the first side.

5. The delivery tool of claim 4, wherein one or more structural members of the plurality of structural members comprises a gripping feature.

6. The delivery tool of claim 5, wherein the gripping feature includes at least one of a protrusion, a groove, or a roughened surface disposed on a surface of the structural member.

7. The delivery tool of claim 2, wherein the longitudinal member comprises a first lateral edge and a second lateral edge opposite the first lateral edge, a first set of the plurality of structural members is distributed longitudinally along the first lateral edge, and a second set of the plurality of structural members is distributed longitudinally along the second lateral edge opposite the first set of the plurality of structural members.

8. The delivery tool of claim 7, wherein the first set of the plurality of structural members comprise a first set of T-shaped members and the second set of the plurality of structural members comprise a second set of T-shaped members.

9. The delivery tool of claim 1, wherein the tool body comprises at least one of polypropylene, polyethylene, acrylonitrile butadiene styrene, or Nitinol.

10. The delivery tool of claim 1, further comprising a lead retention feature disposed at the proximal tool end of the delivery tool and coupled to the tool body, the lead retention feature adapted to engage a portion of the paddle lead body.

11. The delivery tool of claim 10, wherein the lead retention feature comprises:
a lead retention feature body adapted to receive the portion of the paddle lead body therethrough, the lead retention feature body defining a hole;
a tab comprising a protrusion shaped to be inserted into the hole; and
a hinge coupling the tab to the lead retention feature body, the lead retention feature adapted to transition between an engaged configuration in which the protrusion is inserted into the hole and a disengaged configuration in which the protrusion is removed from the hole.

12. The delivery tool of claim 10, wherein the lead retention feature comprises a plurality of walls defining each of an inlet, an outlet, and a lead path extending between the inlet and the outlet, the lead retention feature adapted to retain the portion of the lead body by inserting the portion of the lead body between the inlet and the outlet such that the paddle lead body follows the path defined therebetween.

13. The delivery tool of claim 1 further comprising a handle disposed at the proximal tool end and coupled to the tool body.

14. The delivery tool of claim 1, further comprising a paddle retention feature disposed at the distal tool end and coupled to the tool body, the paddle retention feature adapted to receive the paddle electrode array.

15. The delivery tool of claim 14, wherein the paddle retention feature defines a slot sized to receive the paddle electrode array and to positively retain the paddle electrode array by an interference fit.

16. A delivery tool for use in implanting a paddle lead, the delivery tool having a proximal tool end and a distal tool end opposite the proximal tool end and the paddle lead including a paddle electrode array disposed at a distal end of a paddle lead body, the delivery tool comprising:
a tool body extending between the proximal end and the distal end, the tool body adapted to receive the paddle lead body, the tool body comprising a plurality of structural members adapted to have a first resistance to bending of the tool body in a first plane and to have a second resistance, less than the first resistance, to bending along a second plane perpendicular to the first plane.

17. The delivery tool of claim 16, further comprising a lead retention feature disposed at the proximal tool end and coupled to the tool body, the lead retention feature adapted to retain and fix the position of a portion of the paddle lead relative to the tool body.

18. The delivery tool of claim 16, further comprising a paddle retention feature disposed at the distal tool end and adapted to retain the paddle electrode array.

19. The delivery tool of claim 16, wherein the plurality of structural members comprises:
a first set of structural members disposed in a first section of the tool body adapted to have a third resistance to bending in a first bending direction along the second plane; and
a second set of structural members disposed in a second section of the tool body proximal the first section, the second set of structural members adapted to have a fourth resistance to bending in a second bending direction opposite the first bending direction, each of the third and fourth resistances being less than the first resistance.

20. The delivery tool of claim 16, wherein the plurality of structural members is longitudinally distributed along the tool body and a bending range of the tool body along the second plane is limited by contact between adjacent structural members.

* * * * *